US010485763B2

(12) United States Patent
Lee et al.

(10) Patent No.: US 10,485,763 B2
(45) Date of Patent: Nov. 26, 2019

(54) COMPOSITION FOR TRANSARTERIAL CHEMOEMBOLIZATION, COMPRISING FIRST AND SECOND BIODEGRADABLE MICROBEADS, AND PREPARATION METHOD THEREFOR

(71) Applicant: UTAH-INHA DDS & ADVANCED THERAPEUTICS RESEARCH CENTER, Incheon (KR)

(72) Inventors: Don Haeng Lee, Seoul (KR); Young Hwan Park, Gangwon-do (KR); Se Yoon Kim, Gyeonggi-do (KR); Yixian Li, Incheon (KR)

(73) Assignee: UTAH-INHA DDS & ADVANCED THERAPEUTICS RESEARCH CEN, Incheon (KR)

( * ) Notice: Subject to any disclaimer, the term of this patent is extended or adjusted under 35 U.S.C. 154(b) by 11 days.

(21) Appl. No.: 15/310,281

(22) PCT Filed: May 14, 2015

(86) PCT No.: PCT/KR2015/004859
§ 371 (c)(1),
(2) Date: Nov. 10, 2016

(87) PCT Pub. No.: WO2015/174763
PCT Pub. Date: Nov. 19, 2015

(65) Prior Publication Data
US 2017/0165202 A1    Jun. 15, 2017

(30) Foreign Application Priority Data
May 14, 2014 (KR) .................. 10-2014-0057752

(51) Int. Cl.
A61K 31/4745 (2006.01)
A61K 9/16 (2006.01)

(52) U.S. Cl.
CPC .......... A61K 9/1658 (2013.01); A61K 9/1652 (2013.01); A61K 31/4745 (2013.01)

(58) Field of Classification Search
CPC . A61K 9/1658; A61K 31/4745; A61K 9/1652
See application file for complete search history.

(56) References Cited

U.S. PATENT DOCUMENTS

| | | | |
|---|---|---|---|
| 5,041,292 A | 8/1991 | Feijen | |
| 5,932,248 A * | 8/1999 | Chen | A61K 9/1652 424/484 |
| 7,442,385 B2 | 10/2008 | Lewis et al. | 424/426 |
| 2004/0161466 A1 | 8/2004 | Lewis et al. | 424/489 |

FOREIGN PATENT DOCUMENTS

| | | | |
|---|---|---|---|
| CN | 1139380 A | 1/1997 | |
| JP | 2-188534 | 7/1990 | |
| JP | 9-505059 | 5/1997 | |
| KR | 10-2013-0139303 | 11/2013 | ............... A61K 9/16 |
| KR | 10-2013-0139304 | 11/2013 | ............... A61K 9/16 |
| WO | WO-9513798 A1 | 5/1995 | |
| WO | WO 2012/073188 | 6/2012 | |

OTHER PUBLICATIONS

US 5,849,884 A, 12/1998, Woiszwillo et al. (withdrawn)
International Search Report (ISR) in PCT/KR2015/004859, dated Sep. 4, 2015 published in WO 2015/174763.
Chen, Y., et al. (1994). "Synthesis of albumin-dextran sulfate microspheres possessing favourable loading and release characteristics for the anticancer drug doxorubicin". *Journal of Controlled Release*. 31:49-54.
Cremers, H.F.M. et al., (1990). "Albumin-heparin microspheres as carriers for cytostatic agents". *Journal of Controlled Release*. 11:167-179.
Ginty, P.J. et al., (2008). "Controlling protein release from scaffolds using polymer blends and composites". *European Journal of Pharmaceutics and Biopharmaceutics*. 68:82-89.
Takka, S. et al., (2001). "Effect of anionic polymers on the release of propranolol hydrochloride from matrix tablets" *European Journal of Pharmaceutics and Biopharmaceutics*. 52:75-82.
Tsuchiya, K., et al., (2000). "Tumor-targeted chemotherapy with smancs in lipiodol for renal cell carcinoma: longer survival with larger size tumors". *Adult Urology*. 55(4):495-500.
Wang, C. et al., (2008). "Pingyangmycin loaded bovine serum albumin microspheres for chemoembolization therapy—in vitro and in vivo studies" *International Journal of Pharmaceutics*. 351:219-226.
Notice of Allowance from corresponding Korean Application No. 10-2014-0057752 dated Mar. 29, 2016.
Office Action from corresponding Japanese Application No. 2016-567527 dated Aug. 8, 2017.
Extended European Search Report from corresponding European Application No. 15740074.5 dated May 30, 2017.
Takka, et al.; "Effect of anionic polymers on the release of propranolol hydrochloride from matrix tables", European Journal of Pharmaceutics and Biopharmaceutics, 2001, vol. 52, p. 75-82.

(Continued)

Primary Examiner — Daniel M Podgorski
(74) Attorney, Agent, or Firm — Harness, Dickey & Pierce, P.L.C.

(57) ABSTRACT

The present invention provides: a composition for transarterial chemoembolization, comprising two types of biodegradable microbeads having different anticancer drug release characteristics; and a preparation method therefor. According to the present invention, a composition for transarterial chemoembolization exhibiting a desired anticancer drug release characteristic can be effectively prepared by controlling the mixing ratio of first and second biodegradable microbeads. Therefore, the present invention can be usefully applied to the transarterial chemoembolization of liver cancer.

7 Claims, 10 Drawing Sheets

(56) References Cited

OTHER PUBLICATIONS

Ginty et al.; "Controlling protein release from scaffolds using polymer blends and composites", European Journal of Pharmaceutics and Biopharmaceutics, 2008, vol. 68, p. 82-89.
Cremers et al.; "Preparation and characterization of albumin-heparin microspheres", Biomaterials, 1994, vol. 15(1), p. 38-48.
Cremers et al.; "Adriamycin loading and release characteristics of albumin-heparin conjugate microspheres", Journal of Controlled Release, 1994, vol. 29(1-2), p. 143-155.
Cremers et al.; "Degradation and intrahepatic compatibility of albumin-heparin conjugate microspheres", Biomaterials, 1994, vol. 15(8), p. 577-585.q.
Ghandehari et al.; "Review of Drug Delivery Systems in Cancer Therapy", vol. 1. 98, No. 3, Aug. 27, 2004, p. 457, Book Review dated May 2, 2004.
Office Action from corresponding Chinese Patent Application No. 201580026221.9, dated Feb. 15, 2019.

* cited by examiner

COMPOSITION FOR TRANSARTERIAL CHEMOEMBOLIZATION, COMPRISING FIRST AND SECOND BIODEGRADABLE MICROBEADS, AND PREPARATION METHOD THEREFOR

CROSS-REFERENCE TO RELATED APPLICATIONS

This application is a national phase application of PCT Application No. PCT/KR2015/004859, filed on May 14, 2015, which claims the benefit and priority to Korean Patent Application No. 10-2014-0057752, filed May 14, 2014. The entire disclosures of the applications identified in this paragraph are incorporated herein by references.

FIELD

The present invention relates to a composition for transarterial chemoembolization containing first and second biodegradable microbeads with different anticancer drug release characteristics at a predetermined ratio, and to a method for preparing the same.

BACKGROUND

Recently developed imaging technologies can locate cancer that is hiding in the body, and thus the cancer can be removed by several methods, such as radiation irradiation and endoscopy operation. However, even though the exact location of the cancer is found, the surgical exclusion of the cancer is impossible due to several reasons, such as the cancer spreading out all over the whole organ or adjoining to another organ. Liver cancer, pancreatic cancer, or the like, even though detected, cannot be radically cured through surgical operation.

Currently, transarterial chemoembolization (TACE), which is most commonly done in the treatment of a liver tumor, is a treatment wherein an anticancer drug is administered to the artery, which supplies nutrition to the liver tumor, and then the blood vessel is blocked. Liver tissues receive oxygen and nutrients through the portal vein, which turns around the small intestine and large intestine, and the hepatic artery, which comes out directly from the main artery. Normal liver tissues mainly receive blood from the portal vein, and the tumor tissues mainly receive blood from the hepatic artery. Therefore, in cases where an anticancer drug is administered to the hepatic artery, which supplies nutrition to the tumor, and then the blood vein is blocked, only the tumor can be selectively necrotized without harming normal liver tissues. Such a treatment has many advantages, such as having no restrictions according to the progression of cancer and thus having a wide range of applications, and having a few limitations in the objects of the treatment, and thus currently makes a large contribution on the improvement in the cure rate of the liver cancer. As for chemoembolization, a catheter is first inserted into the femoral artery in the groin and approaches the hepatic artery, and then a vascular contrast medium is injected to obtain information necessary for the treatment, such as positions, sizes, and blood supply aspects of tumors. When the treatment protocol is decided, a thin tube with a thickness of about 1 mm is inserted into the catheter, and then the artery to be targeted is found, followed by surgical operation.

Currently, representatively, hepatic embolization using lipiodol has been clinically applied most frequently, and a significant number of patent technologies using the hepatic embolization have also been reported. Lipiodol contains a lot of iodine as a constituent element, and thus allows CT imaging, thereby providing a convenient surgical procedure. However, in order to load doxorubicin, an injection in which a drug is dissolved needs to be shaken and mixed with oily lipiodol immediately before the surgical operation. In addition, it has been clinically reported that after the surgical operation, the doxorubicin dissolved in an aqueous phase does not accumulate in the liver cancer site, but promptly leaks into the body blood, thereby failing to obtain a sufficient anticancer effect and causing a considerable side effect to patients.

U.S. Pat. No. 7,442,385 discloses a method wherein, after polyvinylalcohol (PVA) is cross-linked to prepare micro-sized particles, doxorubicin as a cancer drug is adsorbed onto a surface of beads via an electric attraction and then transferred to the liver cancer site, thereby attaining both a sustained release of anticancer drug and an embolization effect. For achieving this, during a cross-linkage procedure of polyvinylalcohol, 2-acrylamido-2-methylpropane sulfonic acid (AMPS), which is an anionic monomer, is covalently linked to the end of the cross-linkage to modify the polymer, thereby allowing the polymer to adsorb a cationic drug, such as doxorubicin. However, according to the hepatic embolization using polyvinylalcohol, cross-liked PVA does not degrade in the body, and thus, after the necrotization of the liver tumor, PVA beads were irregularly diffused in the body, causing an inflammation or more unfortunately, the PVA beads go down the blood vessel and spreads into another organ, causing cerebrovascular disease. Therefore, a drug delivery system capable of achieving both a function as an anticancer drug carrier and a vascular embolization function to solve the foregoing problems is required.

Due to these requirements, the present inventors have developed albumin/dextran sulfate beads (Korean Patent Application No. 10-2013-0139303) and albumin/glycosaminoglycan beads (Korean Patent Application No. 10-2013-0139304), which solved problems of existing microbeads for cancer local treatment. The microbeads are safe to the human body when applied to the human body since the microbeads are prepared from albumin, as a biocompatible material, and an anionic polymer, and can effectively inhibit the growth of tumors by effectively blocking the blood vessel that supplies nutrients to the liver tumor and can continuously release an anticancer drug adsorbed onto the surfaces of the beads.

Meanwhile, the drug release characteristics of microbeads for transarterial chemoembolization are different for the respective beads, and, due to a small amount of clinical results, statistic results showing whether a fast release rate is more effective or a slow release rate is more effective are insufficient. Further, the drug release rate also needs to be controlled depending on the size of tumors and the progression of cancers.

Throughout the entire specification, many papers, and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION

Technical Problem

The present inventors have researched and endeavored to develop techniques to effectively control the release rate of a drug from microbeads for transarterial chemoembolization according to the use environment and use purpose of the microbeads. As a result, the present inventors have found that the drug release characteristics of an albumin/dextran sulfate bead and an albumin/glycosaminoglycan bead are different from each other, and have verified that, when the two beads are mixed at a particular ratio for use, the drug release rate is controlled according to the mixing ratio, and then have completed the present invention.

Therefore, an aspect of the present invention is to provide a composition for transarterial chemoembolization containing the two kinds of microbeads.

Another aspect of the present invention is to provide a use of the two kinds of microbeads for preparing a composition for transarterial chemoembolization.

Still another aspect of the present invention is to provide a method for preparing the composition for transarterial chemoembolization.

Still another aspect of the present invention is to provide a method for treating cancer by administering the two kinds of microbeads having a drug adsorbed onto a surface thereof.

Other purposes and advantages of the present invention will become more obvious with the following detailed description of the invention, claims, and drawings.

Technical Solution

In accordance with an aspect of the present invention, there is provided a composition for transarterial chemoembolization, containing: first biodegradable microbeads comprising: albumin, which is cross-linked to form a shape of a bead; and dextran sulfate, as an anionic polymer, contained in the albumin cross-linked product; second biodegradable microbeads comprising: albumin, which is cross-linked to form a shape of a bead; and a glycosaminoglycan-based polymer, as an anionic polymer, contained in the albumin cross-linked product, wherein the first and second biodegradable microbeads allow an anticancer drug to be adsorbed onto a surface of the microbeads through an electrostatic attraction of the anionic polymers contained therein.

In accordance with another aspect of the present invention, there is provided a use of the first and second biodegradable microbeads for preparing the composition for transarterial chemoembolization.

The present inventors have researched and endeavored to develop techniques to effectively control the release rate of a drug from microbeads for transarterial chemoembolization according to the use environment and use purpose of the microbeads. As a result, the present inventors have found that the drug release characteristics of an albumin/dextran sulfate bead and an albumin/glycosaminoglycan bead are different from each other, and have verified that, when the two beads are mixed at a particular ratio for use, the drug release rate is controlled according to the mixing ratio.

According to an embodiment of the present invention, the composition of the present invention containing first and second biodegradable microbeads can release an anticancer drug around when administered into the body, and here, the release rate of the anticancer drug is changed according to the mixing ratio of the first and second biodegradable microbeads contained in the composition.

As verified through the following examples, the release rate of an anticancer drug by the albumin/dextran sulfate beads (the first biodegradable microbeads) was remarkably slower than that by the albumin/glycosaminoglycan beads (the second biodegradable microbeads), and a mixture of these microbeads showed different release (dissolution) characteristics of an anticancer drug according the mixing ratio thereof (see FIGS. 6 to 10). Therefore, the release (dissolution) rate of an anticancer drug by the composition can be controlled by adjusting the mixing ratio of the first and second biodegradable microbeads.

According to an embodiment of the present invention, the ratio of the first biodegradable microbeads and the second biodegradable microbeads contained in the composition of the present invention is 0.01-99.99:99.99-0.01 (v/v %).

According to an embodiment of the present invention, the release rate of an anticancer drug by the composition of the present invention is increased according to an increased ratio of the second biodegradable microbeads to the first biodegradable microbeads.

The composition for transarterial chemoembolization of the present invention may be administered into the body for the treatment of solid cancers. For example, the composition of the present invention may be administered into the body for transcatheter arterial chemoembolization. As for the solid cancer to which embolization is applicable besides the treatment of liver cancer, rectal cell carcinoma may be treated through rectal artery (K. Tsuchiya, *Urology*. April; 55(4): 495-500 (2000)).

According to an embodiment of the present invention, the composition of the present invention may be implemented such that the first and second biodegradable microbeads are packaged in a suitable container (e. g., vial). Here, the biodegradable microbeads of the present invention may be packaged in a vial together with a solution (wet type), or the biodegradable microbeads may be pulverized, and then packaged in a vial (dry type). In addition, the first and second biodegradable microbeads may be present in a mixed state in a container, and may be selectively present in separately compartmented spaces.

Hereinafter, the first and second biodegradable microbeads will be described in detail. The description of the microbeads is disclosed in Korean Patent Application Nos. 10-2013-0139303 and 10-2013-0139304, the literature of which are incorporated herein by reference.

The first biodegradable microbeads include, as constituent ingredients, albumin, and dextran sulfate. The albumin is cross-linked to serve as a support to form and support a shape of the microbead. The dextran sulfate, as an anionic polymer, is contained in the cross-linked albumin to allow an anticancer drug to be adsorbed onto a surface of the bead. Since the albumin and dextran sulfate are biocompatible polymer materials and can be degraded in the body, both can solve the problems of an existing bead using polyvinyl alcohol, caused by non-degradability thereof in the body, for example, polyvinyl alcohol spreads irregularly to cause inflammation, or spreads into other organs through blood vessels to cause cerebral thrombosis.

The second biodegradable microbeads include, as constituent ingredients, albumin, and a glycosaminoglycan-based polymer. The albumin is cross-linked to serve as a support to form and support the shape of the microbead, like in the first biodegradable microbeads. The glycosaminoglycan-based polymer, as an anionic polymer, is contained in the cross-linked albumin to allow an anticancer drug to be adsorbed onto a surface of the bead. Since the albumin and glycosaminoglycan-based polymer are biocompatible polymer materials and can be degraded in the body, both can solve the problems of an existing bead using polyvinyl alcohol, caused by non-degradability thereof in the body, for example, polyvinyl alcohol spreads irregularly to cause inflammation, or spreads into other organs through blood vessels to cause cerebral thrombosis, like in the first biodegradable microbead.

According to an embodiment of the present invention, the anionic polymer of the first and/or second biodegradable microbeads is amide-linked with the cross-linked albumin. In this case, the albumin is amide-linked with a carboxyl group or an amine group of the anionic polymer while being cross-linked, thereby serving as a support to form and support a shape of the microbead. The anionic polymer is amide-linked with an amine group or carboxyl group of the albumin, and serves to allow the anticancer drug to be adsorbed onto a surface of the beads.

According to an embodiment of the present invention, the second biodegradable microbead includes an albumin-glycosaminoglycan conjugate formed by an amide linkage of the cross-linked albumin and the glycosaminoglycan-based polymer as an anionic polymer.

As used herein, the term "biodegradable" refers to being capable of degrading when exposed to a physiological solution, and for example, refers to being capable of degrading by the body fluid or microorganisms in the living bodies of mammals including a human being.

According to an embodiment of the present invention, the albumin is a protein that is widely distributed in living cells or the body fluid, and includes animal albumins and vegetable albumins.

According to a particular embodiment, the animal albumin includes ovalbumin, serum albumin, lactalbumin, and miogen, and the vegetable albumins include leucosin (barely seeds), legumelin (peas), and lysine (castor seeds). The albumin also includes albumin variants.

According to an embodiment of the present invention, the glycosaminoglycan-based polymer is selected from the group consisting of chondroitin sulfate, dermatan sulfate, keratan sulfate, heparan sulfate, heparin, and hyaluronan.

According to another embodiment of the present invention, the cross-linkage of the albumin is achieved by thermal cross-linkage or an aldehyde-based cross-linking agent.

According to a particular embodiment, the aldehyde-based cross-linking agent is selected from the group consisting of glutaraldehyde, formaldehyde, dialdehyde starch, succinate aldehyde, acryl aldehyde, oxal aldehyde, 2-methylacrylaldehyde, and 2-oxopropanal.

According to one embodiment of the present invention, the first and second biodegradable microbeads may allow 10-100 mg of an anticancer drug to be adsorbed onto 1 ml of the microbeads.

The anticancer drug adsorptivity of the biodegradable microbeads is 20-60 mg per 1 ml of microbeads for one specific embodiment, 20-55 mg per 1 ml of microbeads for another specific embodiment, and 20-50 mg per 1 ml of microbeads for still another specific embodiment.

According to an embodiment of the present invention, the first and second biodegradable microbeads further comprise an anticancer drug adsorbed onto a bead surface by an electrostatic attraction with the anionic polymer.

According to a particular embodiment, the anticancer drug is an anthracycline-based anticancer drug. Examples of the anthracycline-based anticancer drug may include doxorubicin, daunorubicin, epirubicin, idarubicin, gemcitabine, mitoxantrone, pirarubicin, and valrubicin.

In another specific embodiment, the anticancer drug is irinotecan.

In accordance with another aspect of the present invention, there is provided a method for preparing a composition for transarterial chemoembolization, the method including:

(a) preparing first biodegradable microbeads in which albumin is cross-linked and dextran sulfate is contained in the albumin cross-linked product, by cross-linking micro-sized bubbles formed by emulsifying a solution for preparing beads, in which albumin and dextran sulfate as an anionic polymer are dissolved;

(b) preparing second biodegradable microbeads in which albumin is cross-linked and a glycosaminoglycan-based polymer is contained in the albumin cross-linked product, by cross-linking micro-sized bubbles formed by emulsifying a solution for preparing beads, in which albumin and a glycosaminoglycan-based polymer as an anionic polymer are dissolved; and (c) mixing the first and second biodegradable microbeads at a predetermined ratio, followed by packaging in a container, wherein the anticancer drug release rate of the composition is controlled according to the mixing ratio of the first and second biodegradable beads.

According to an embodiment of the present invention, the method of the present invention further includes a step for, after step (a) and/or step (b), bringing an anticancer drug into contact with the prepared first and second biodegradable microbeads to allow the anticancer drug to be adsorbed onto a surface of the microbeads by an electrostatic attraction of the anionic polymers of the microbeads.

According to another embodiment of the present invention, the method of the present invention further comprises, a step for, after step (c), bringing an anticancer drug into contact with the first and second biodegradable microbeads packaged in the container to allow the anticancer drug to be adsorbed onto a surface of the microbeads by an electrostatic attraction of the anionic polymers of the microbeads. Here, the adsorption of the anticancer drug may be performed while the biodegradable microbeads are packaged in the container, or may be performed in a separate container after the microbeads are taken out of the container.

According to an embodiment of the present invention, the emulsifying of the solution for preparing beads in steps (a) and (b) is performed using an organic solvent containing natural oil or a viscosity-increasing agent.

Examples of usable natural oil may be MCT oil, cottonseed oil, corn oil, almond oil, apricot oil, avocado oil, babassu oil, chamomile oil, canola oil, cocoa butter oil, coconut oil, cod-liver oil, coffee oil, fish oil, flax seed oil, jojoba oil, gourd oil, grape seed oil, hazelnut oil, lavender oil, lemon oil, mango seed oil, orange oil, olive oil, mink oil, palm tree oil, rosemary oil, sesame oil, shea butter oil, bean oil, sunflower oil, walnut oil, and the like.

Examples of the usable organic solvent may be acetone, ethanol, butyl acetate, and the like. The organic solvent may include a viscosity-increasing agent for providing appropriate viscosity. Examples of the viscosity-increasing agent may be cellulose-based polymers, such as hydroxymethyl cellulose, hydroxypropyl methyl cellulose, and cellulose acetate butyrate.

According to one embodiment of the present invention, the micro-sized bubbles in steps (a) and (b) may be formed using a microfluidic system or an encapsulator. The microfluidic system is a method wherein beads are prepared using a micro-structured chip. After a smaller tube is positioned inside a larger tube, an aqueous phase and an oil phase are allowed to flow through the tubes in opposite directions, thereby forming beads by tensile strengths therebetween. That is, when the solution for preparing beads as an inner fluid and the natural oil or organic solvent (collection solution) as an outer fluid are allowed to flow, the beads are formed by tension. The beads are again collected into the collection solution, and then the beads may be prepared through a cross-linking reaction.

The encapsulation is similar to electrospinning, and is characterized in that an electric field, which is formed between a nozzle and a collection solution, finely splits water drops generated by tension, thereby dispersing very small-sized droplets. The solution for preparing beads is transferred into a syringe corresponding to the volume thereof, and the syringe is mounted on a syringe pump, and then connected with an encapsulator. In addition, the collection solution is also transferred into a dish corresponding to the volume thereof, and then positioned on a stirrer. The environment of the encapsulator is appropriately set, and then the solution for preparing beads is sprayed to the collection solution to form bubbles. Preferably, the conditions of the encapsulator are a flow rate of 1-5 ml/min, applied electric power of 1,000-3,000 V, ultrasonic wave of 2,000-6,000 Hz, and a revolution number of 100 rpm or less. The size of a release nozzle is selected according to the size of beads to be prepared.

According to another embodiment of the present invention, the micro-sized bubbles in steps (a) and (b) may be prepared by an emulsifying method wherein a solution for preparing beads is mixed with a collection solution, and then the mixture is stirred at a proper revolution number. Here, the size of the beads depends on the revolution number and the stirring time. When appropriate-sized bubbles are formed, the bubbles are cross-linked to form microbeads.

According to an embodiment of the present invention, the stirring continues to maintain a cross-linkage reaction of albumin until the cross-linking reaction of albumin is completed, and upon completion of the reaction, the beads are washed several times using a large amount of acetone or ethanol for the washing of the collection solution.

According to an embodiment of the present invention, the cross-linking is performed using an aldehyde-based cross-linking agent or by thermal cross-linkage. In cases where the microbeads of the present invention are prepared by thermal cross-linkage, the microbeads have excellent body compatibility due to the non-use of a chemical cross-linking agent that is harmful to the human body, and may have economic advantages due to the omission of a removing step of the chemical cross-linking agent.

According to an embodiment of the present invention, the temperature for thermal cross-linking temperature is 60° C. or higher (e.g, 60-160° C.) and the time for thermal cross-linking is 1-4 hours.

According to an embodiment of the present invention, the solution for preparing beads in step (b) contains an albumin-glycosaminoglycan conjugate formed by an amide linkage of albumin and a glycosaminoglycan-based polymer. In this case, in step (b), a second biodegradable microbeads in which albumin is cross-linked is prepared by cross-linking micro-sized bubbles formed by emulsifying the albumin-glycosaminoglycan conjugate formed by an amide linkage of albumin and a glycosaminoglycan-based polymer. Therefore, the second biodegradable microbeads containing an albumin-glycosaminoglycan conjugate, in which the cross-linked albumin is amide-linked with a glycosaminoglycan-based polymer.

In step (c), for a desired release rate of an anticancer drug by the composition for transarterial chemoembolization, the first and second biodegradable microbeads are mixed at a predetermined ratio and packaged in a container (e.g., vial). Here, the mixing ratio of the first biodegradable microbeads and the second biodegradable microbeads is 0.01-99.99: 99.99-0.01 (v/v %) on the basis of 100% (v/v).

In accordance with still another aspect of the present invention, there is provided a method for treating cancer, the method including, administering a composition to a patient in need of the composition, the composition containing first biodegradable microbeads and second biodegradable microbeads, the first biodegradable microbeads comprising: albumin, which is cross-linked to form a shape of a bead; and dextran sulfate, as an anionic polymer, contained in the albumin cross-linked product, the second biodegradable microbeads comprising: albumin, which is cross-linked to form a shape of a bead; and a glycosaminoglycan-based polymer, as an anionic polymer, contained in the albumin cross-linked product, wherein an anticancer is adsorbed onto a surface of the first and second biodegradable microbeads through an electrostatic attraction of the anionic polymers contained in the microbeads.

According to the present invention, the composition is administered into a cancer patient, thereby treating cancer through chemoembolization.

According to an embodiment of the present invention, the patient is a liver cancer patient, and the microbeads are administered through the hepatic artery of the patient.

Advantageous Effects

Features and advantages of the present invention are summarized as follows:

(i) The present invention provides a composition for transarterial chemoembolization containing two kinds of biodegradable microbeads with different anticancer drug release characteristics, and to a method for preparing the same.

(ii) According to the present invention, a composition for transarterial chemoembolization can be efficiently produced that exhibits desired anticancer drug release characteristics by adjusting the mixing ratio of the first and second biodegradable microbeads.

(iii) Therefore, the present invention can be favorably utilized for chemoembolization for liver cancer.

MODE FOR CARRYING OUT THE INVENTION

Figure 1:
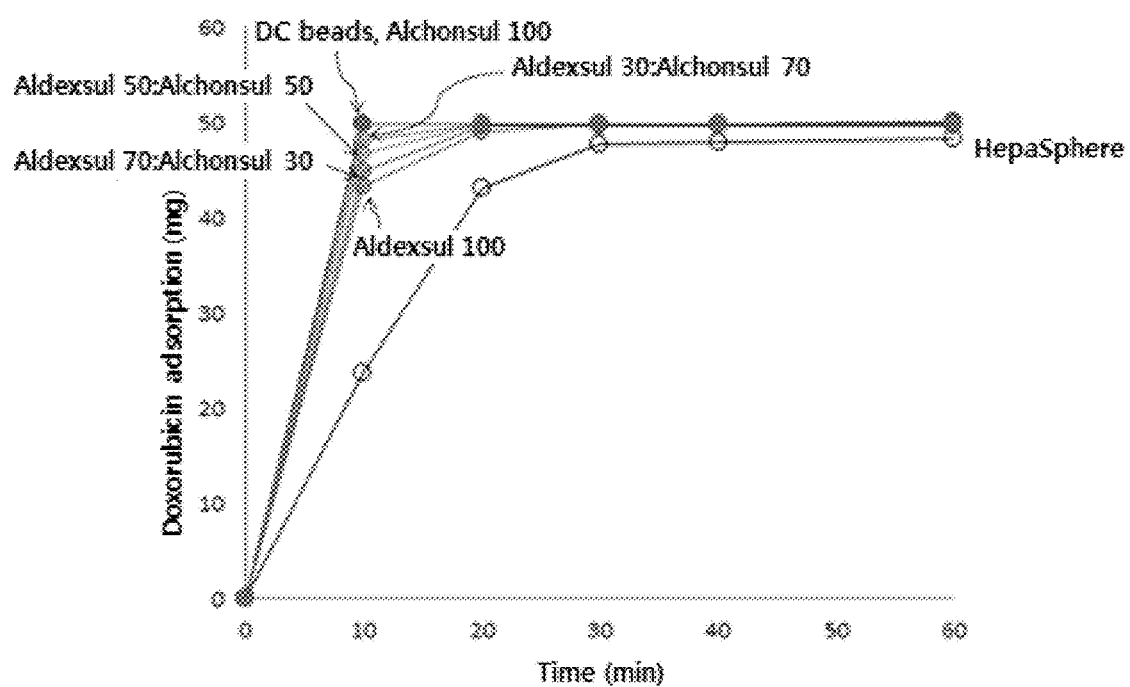
FIG. 1 is a graph showing the anticancer drug adsorption over time of albumin/dextran sulfate beads (aldexsul), albumin/chondroitin sulfate beads (alchonsul), mixed beads thereof, and DC beads and HepaSphere on the market.
Figure 2:
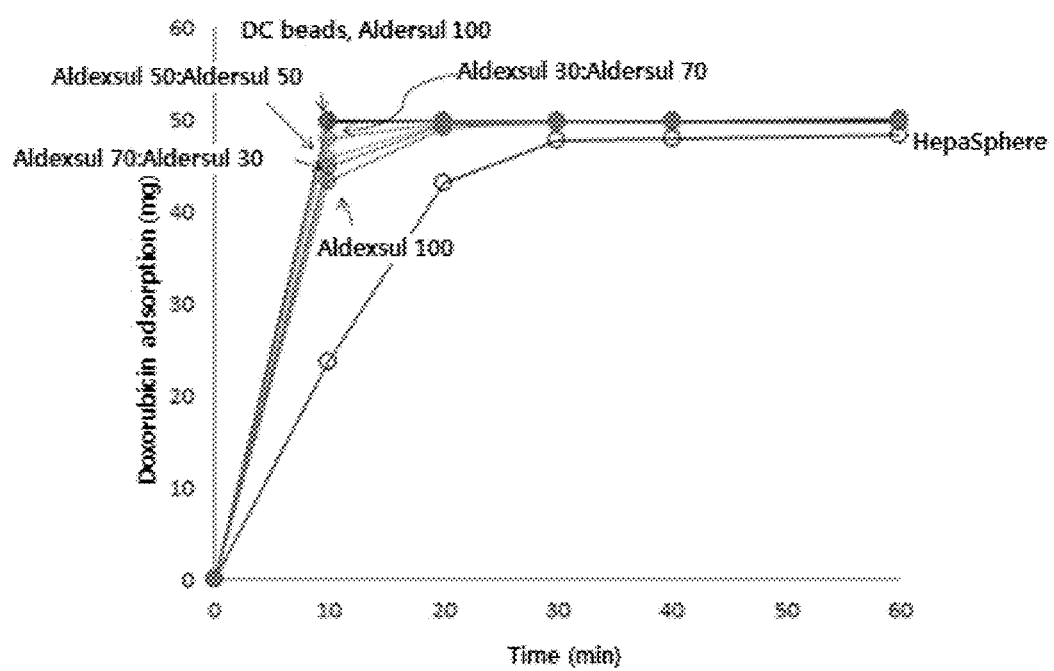
FIG. 2 is a graph showing the anticancer drug adsorption over time of albumin/dextran sulfate beads (aldexsul), albumin/dermatan sulfate beads (aldersul), mixed beads thereof, and DC beads and HepaSphere on the market.
Figure 3:
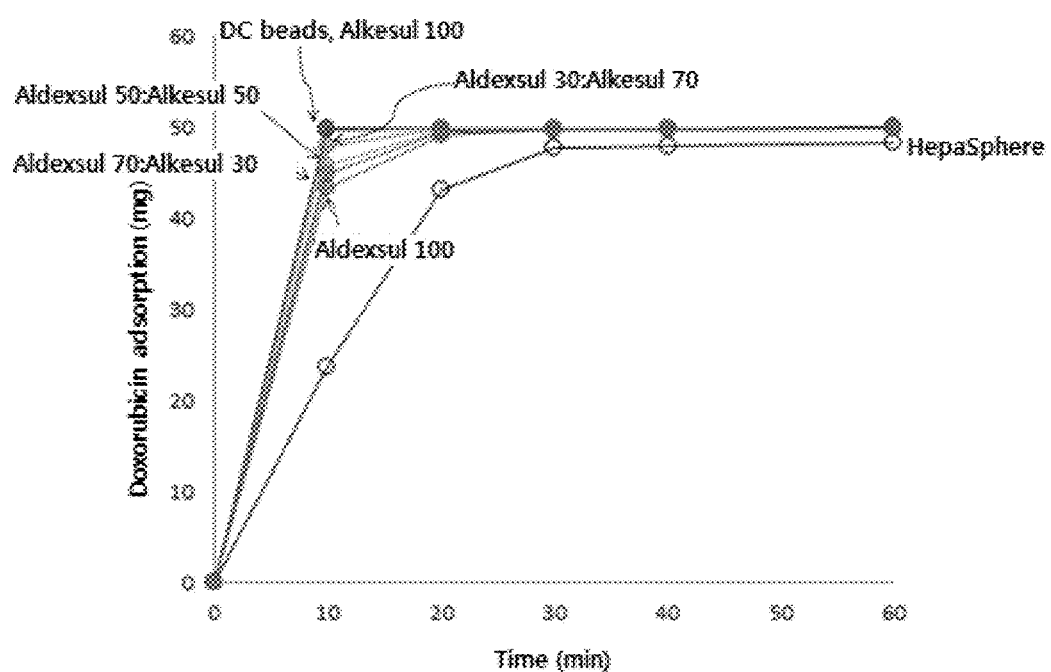
FIG. 3 is a graph showing an anticancer drug adsorption over time of albumin/dextran sulfate beads (aldexsul), albumin/keratan sulfate beads (alkesul), mixed beads thereof, and DC beads and HepaSphere on the market.
Figure 4:
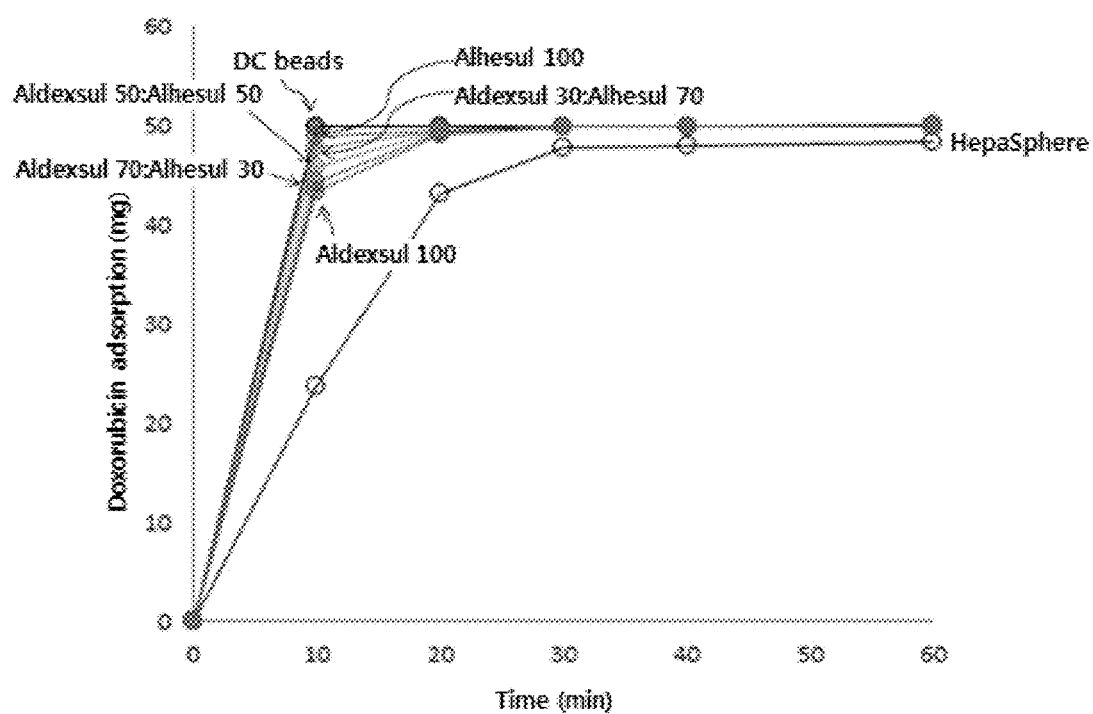
FIG. 4 is a graph showing the anticancer drug adsorption over time of albumin/dextran sulfate beads (aldexsul), albumin/heparan sulfate beads (alhesul), mixed beads thereof, and DC beads and HepaSphere on the market.

Hereinafter, the present invention will be described in detail with reference to examples. These examples are only for illustrating the present invention more specifically, and it will be apparent to those skilled in the art that the scope of the present invention is not limited by these examples.

EXAMPLES

Preparative Example 1: Preparation of Albumin/Dextran Sulfate Beads

Microbeads, in which albumin is cross-linked to form a shape of beads and dextran sulfate is contained in the albumin cross-linked product, were prepared by the following method. The compositions of albumin and an anionic polymer for preparing microbeads are shown in table 1 below.

Microparticles with compositions 1 to 5 above were prepared by using an encapsulator. The preparation conditions were: a flow rate of 1-5 ml/min, applied electric power of 1,000-3,000 V, ultrasonic wave of 2,000-6,000 Hz, and a revolution number of 100 rpm or less. The size of a release nozzle was selected according to the size of beads to be prepared. The solution for preparing beads was transferred into a syringe corresponding to the volume thereof, and the syringe is mounted on a syringe pump. After that, the syringe is connected with an encapsulator (B-390, BUCHI), and the collection solution was transferred into a dish corresponding to the volume thereof, and then placed on a stirrer. After the environment of the encapsulator was set, the solution for preparing beads was sprayed in the collection solution, and then the collection solution was heated at 80-120° C. to be thermally cross-linked, thereby forming beads. The cross-linking time was 2-6 hours. As the collection solution, n-butyl acetate, in which 10% cellulose acetate butyrate was dissolved, or acetone, in which hydroxy propyl methyl cellulose was contained, was used. In example 1 below, the albumin/dextran sulfate beads with composition 1 were used.

Preparative Example 2: Preparation of Albumin/Glycosaminoglycan Beads

For the amide linkage of an amine group ($NH_2$—) of albumin and a carboxyl group (COOH—) of glycosaminoglycan as an anionic polymer, sodium cyanoborohydride (SCBH) or 1-ethyl-3-(3-dimethylamino-propyl)carbodiimide (EDS)/N-hydroxy succinimide (NHS) was used. First, the anionic polymer was activated using SCBH or EDC/NHS, and then linked with albumin with compositions 2 to 5 in table 2 below. After that, the resultant material was dialyzed for 1-2 days to remove unreacted materials, thereby obtaining a solution for preparing beads.

TABLE 1

| W/V % | | Composition 1 | Composition 2 | Composition 3 | Composition 4 | Composition 5 |
|---|---|---|---|---|---|---|
| Albumin | Human serum albumin | 20 | 30 | — | — | 10 |
| | Bovine serum albumin | — | — | 20 | 30 | 10 |
| Anionic polymer | Dextran sulfate | 10 | 10 | 10 | 10 | 10 |

TABLE 2

| W/V % | | Composition 1 | Composition 2 | Composition 3 | Composition 4 | Composition 5 |
|---|---|---|---|---|---|---|
| Albumin | Human serum albumin | 15 | 20 | — | — | 10 |
| | Bovine serum albumin | — | — | 15 | 20 | 10 |
| Anionic polymer | Chondroitin sulfate | 15 | 10 | 15 | 10 | 10 |
| | Dermatan sulfate | 15 | 10 | 15 | 10 | 10 |
| | Keratan sulfate | 15 | 10 | 15 | 10 | 10 |
| | Heparan sulfate | 15 | 10 | 15 | 10 | 10 |
| | Heparin | 15 | 10 | 15 | 10 | 10 |

Microparticles with compositions 1 to 5 above were prepared by using an encapsulator. The preparation conditions were: a flow rate of 1-5 ml/min, applied electric power of 1,000-3,000 V, ultrasonic wave of 2,000-6,000 Hz, and a revolution number of 100 rpm or less. The size of a release nozzle was selected according to the size of beads to be prepared. The solution for preparing beads was transferred into a syringe corresponding to the volume thereof, and the syringe is mounted on a syringe pump. After that, the syringe is connected with an encapsulator (B-390, BUCHI), and the collection solution was transferred into a dish corresponding to the volume thereof, and then placed on a stirrer. After the environment of the encapsulator was set, the solution for preparing beads was sprayed in the collection solution, and then the collection solution was heated at 80-120° C. to be thermally cross-linked, thereby forming beads. The cross-linking time was 2-6 hours. As the collection solution, n-butyl acetate, in which 0% cellulose acetate butyrate was dissolved, or acetone, in which hydroxy propyl methyl cellulose was contained, was used. In example 1 below, the albumin/glycosaminoglycan beads with composition 1 were used.

Example 1: Mixing of Microbeads for Chemoembolization

The albumin/dextran sulfate beads prepared in preparative example 1 had a slow loading rate and a very slow drug dissolution rate, compared with the albumin/glycosaminoglycan beads prepared in preparative example 2. Therefore, the present inventors tried to control the release rate of the drug adsorbed onto the beads by adjusting the mixing ratio of the beads. The compositions of the mixed beads are shown in table 3 below.

long time compared with the other beads, while doxorubicin was adsorbed onto the other beads in similar manners (FIGS. 1 to 5).

Example 3: Doxorubicin Dissolution Test

In order to investigate the drug dissolution behavior, the dissolution test was conducted using a dissolution system. The test method was as follows. 2 ml of beads (albumin/dextran sulfate beads, albumin/glycosaminoglycan beads, mixed beads thereof, DC beads, or HepaSphere) loading 50 mg of the drug through the doxorubicin adsorption test were put in a glass vessel containing 500 ml of a dissolution solution (PBS, pH 7.4), followed by stirring at 50 rpm with incubation at 37° C. The dissolution solution was used without being exchanged, and the supernatant was taken at 10, 20, 30, 40, 60, 90, and 120 minutes, followed by HPLC analysis.

The dissolution results are shown in FIGS. 6 to 10. As shown in the drawings, the anticancer drug dissolution characteristics of the respective microbeads were different. Especially, the anticancer drug dissolution rate of the albumin/dextran sulfate beads was remarkably slow compared with that of the albumin/glycosaminoglycan beads, and the mixed beads of the albumin/dextran sulfate beads and the albumin/glycosaminoglycan beads showed an increasing dissolution rate according to an increased mixing proportion of the albumin/glycosaminoglycan beads (FIGS. 6 to 10).

These results show that the anticancer drug release rate can be freely controlled by adjusting the mixing ratio of the albumin/dextran sulfate beads and the albumin/glycosaminoglycan beads.

Although the present invention has been described in detail with reference to the specific features, it will be

TABLE 3

| | V/V % | Composition 1 | Composition 2 | Composition 3 | Composition 4 | Composition 5 |
|---|---|---|---|---|---|---|
| | Albumin/Dextran sulfate beads | 100 | 70 | 50 | 30 | 0 |
| Glycosamino glycan-based anionic polymer beads | Albumin/Chondroitin sulfate | 0 | 30 | 50 | 70 | 100 |
| | Albumin/Dermatan sulfate | 0 | 30 | 50 | 70 | 100 |
| | Albumin/Keratan sulfate | 0 | 30 | 50 | 70 | 100 |
| | Albumin/Heparan sulfate | 0 | 30 | 50 | 70 | 100 |
| | Albumin/Heparin | 0 | 30 | 50 | 70 | 100 |

Example 2: Doxorubicin Adsorption Test

A doxorubicin adsorption test was conducted as follows. First, 50 mg of doxorubicin was dissolved in 2 ml of distilled water. Then, 2 ml of beads (albumin/dextran sulfate beads, albumin/glycosaminoglycan beads, mixed beads thereof, DC beads, or HepaSphere) were accurately taken according to the mixing ratio, and then put in a doxorubicin solution, followed by mixing. After the mixture was left at room temperature for 10, 20, 30, 40, and 60 minutes, the supernatant was taken, followed by HPLC analysis. The amount of doxorubicin leaking out from 50 mg/2 ml of the doxorubicin solution may be determined by calculating the concentration through the comparison with the previously prepared calibration curve, and such a value was the amount of doxorubicin adsorbed onto the beads.

Figure 5:
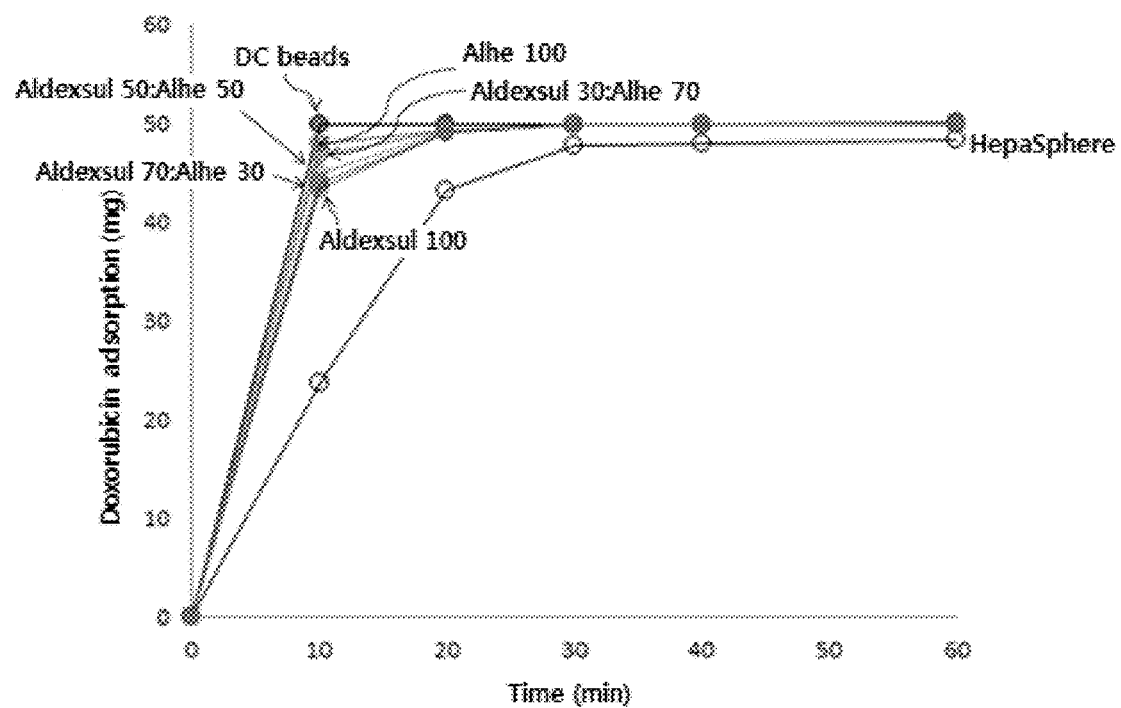
FIG. 5 is a graph showing the anticancer drug adsorption over time of albumin/dextran sulfate beads (aldexsul), albumin/heparin beads (alhe), mixed beads thereof, and DC beads and HepaSphere on the market.
Figure 6:
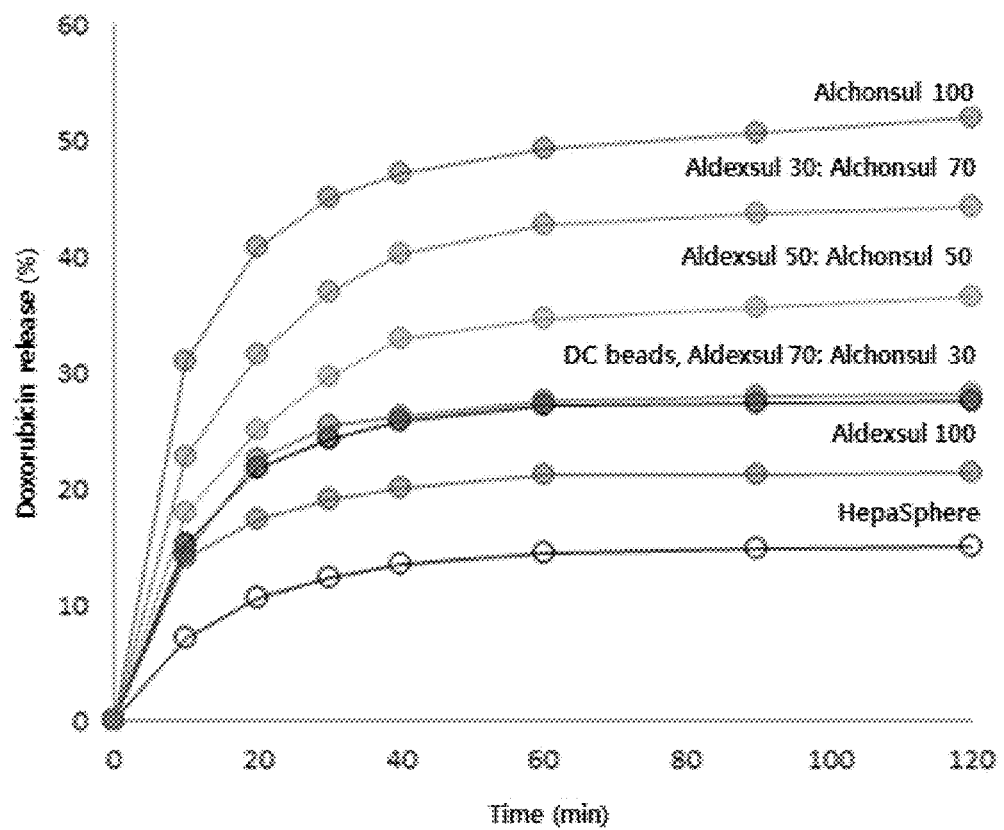
FIG. 6 is a graph showing the anticancer drug release rate over time of albumin/dextran sulfate beads (aldexsul), albumin/chondroitin sulfate beads (alchonsul), mixed beads thereof, and DC beads and HepaSphere on the market.
Figure 7:
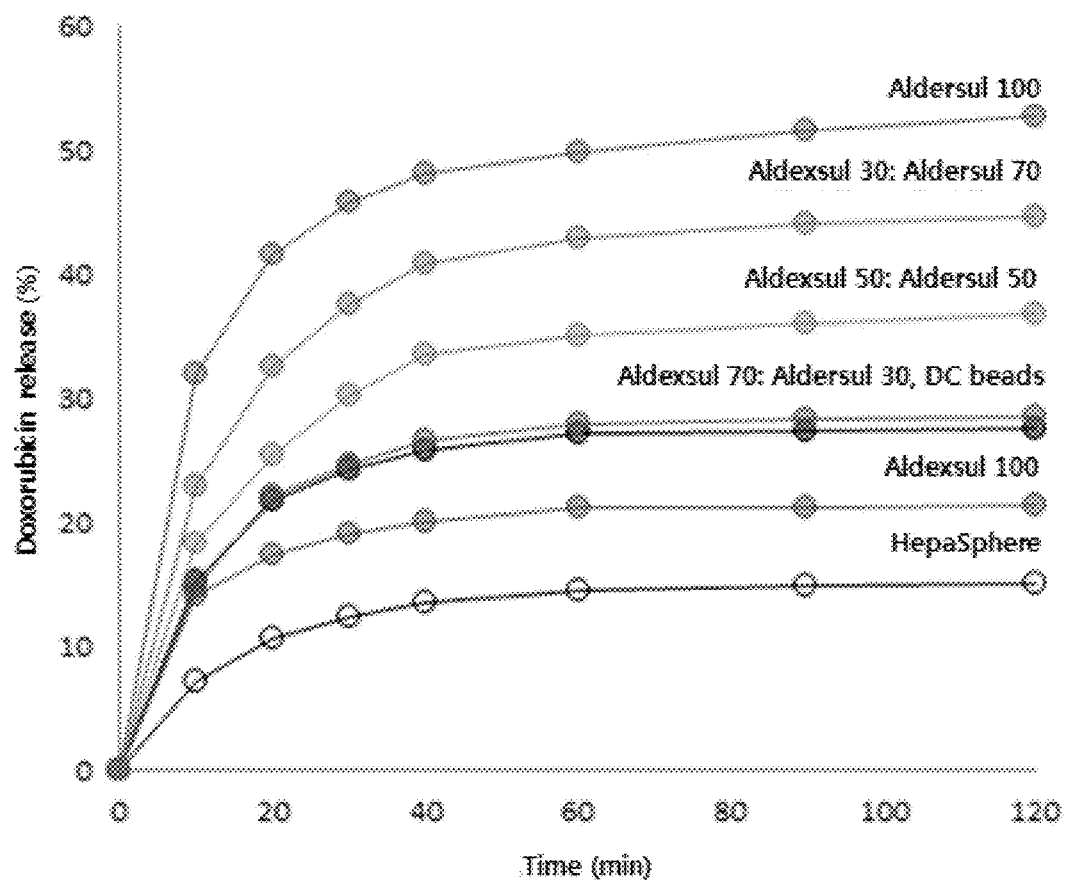
FIG. 7 is a graph showing the anticancer drug release rate over time of albumin/dextran sulfate beads (aldexsul), albumin/dermatan sulfate beads (aldersul), mixed beads thereof, and DC beads and HepaSphere on the market.
Figure 8:
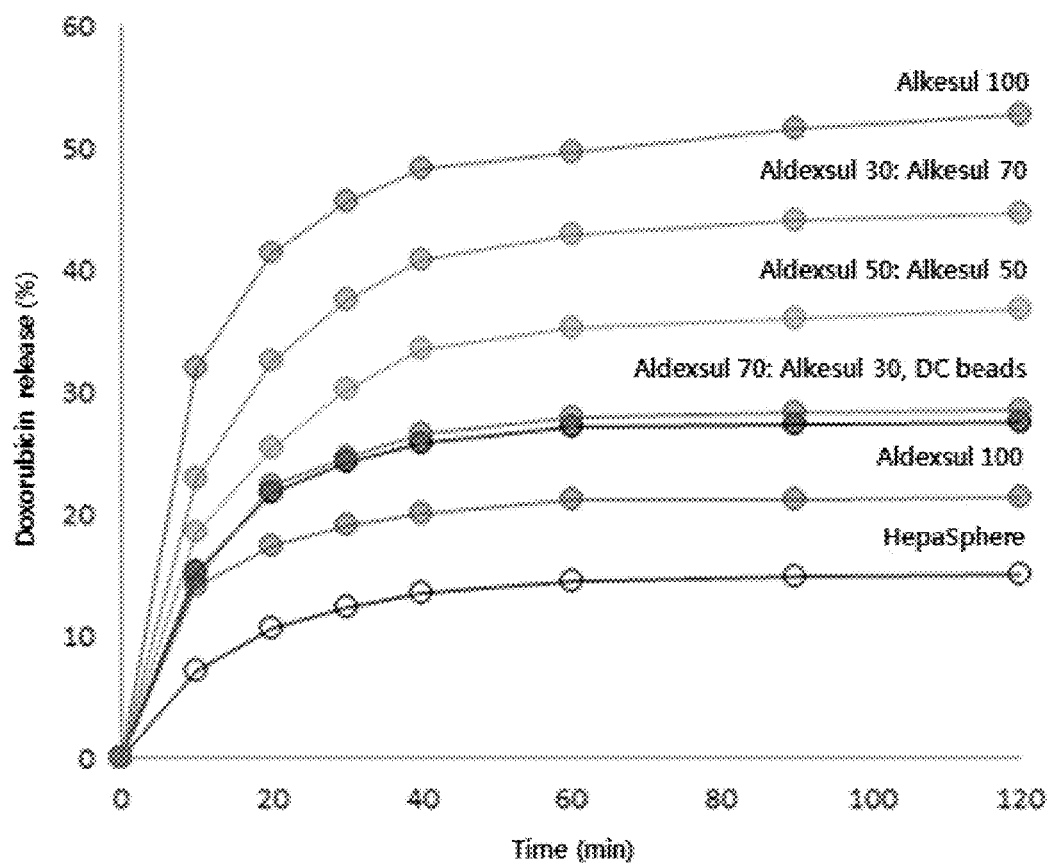
FIG. 8 is a graph showing the anticancer drug release rate over time of albumin/dextran sulfate beads (aldexsul), albumin/keratan sulfate beads (alkesul), mixed beads thereof, and DC beads and HepaSphere on the market.
Figure 9:
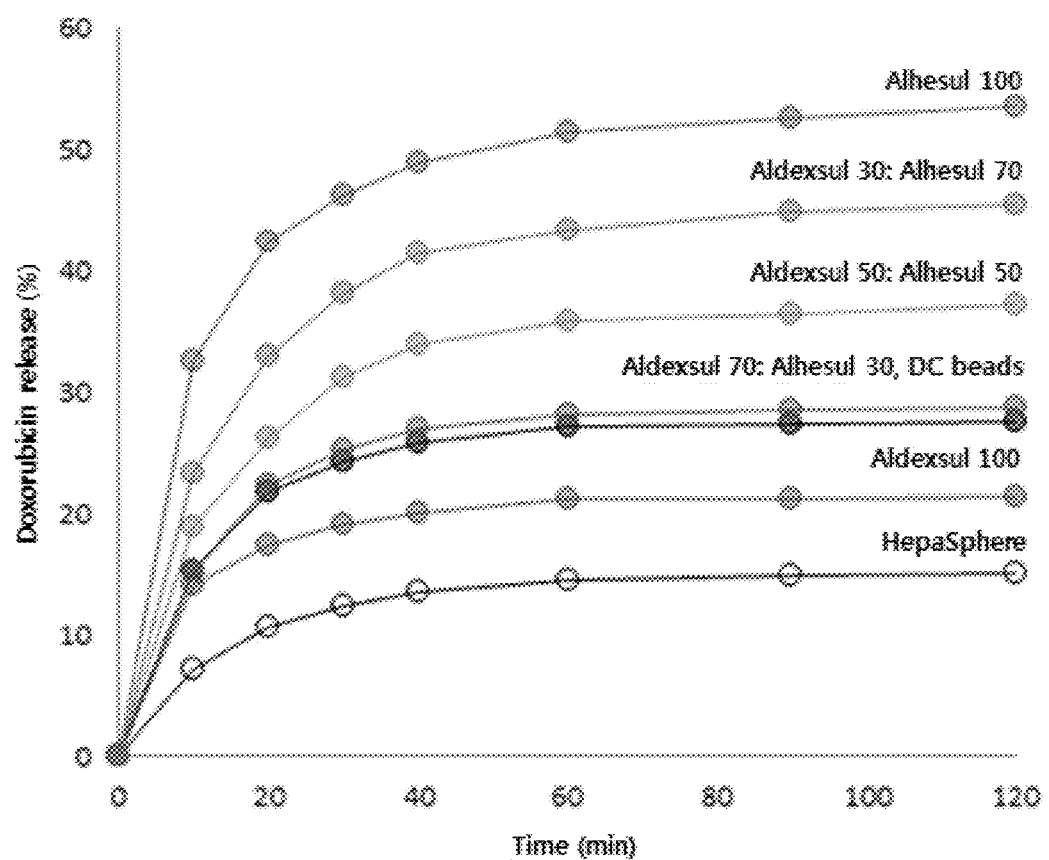
FIG. 9 is a graph showing the anticancer drug release rate over time of albumin/dextran sulfate beads (aldexsul), albumin/heparan sulfate beads (alhesul), mixed beads thereof, and DC beads and HepaSphere on the market.
Figure 10:
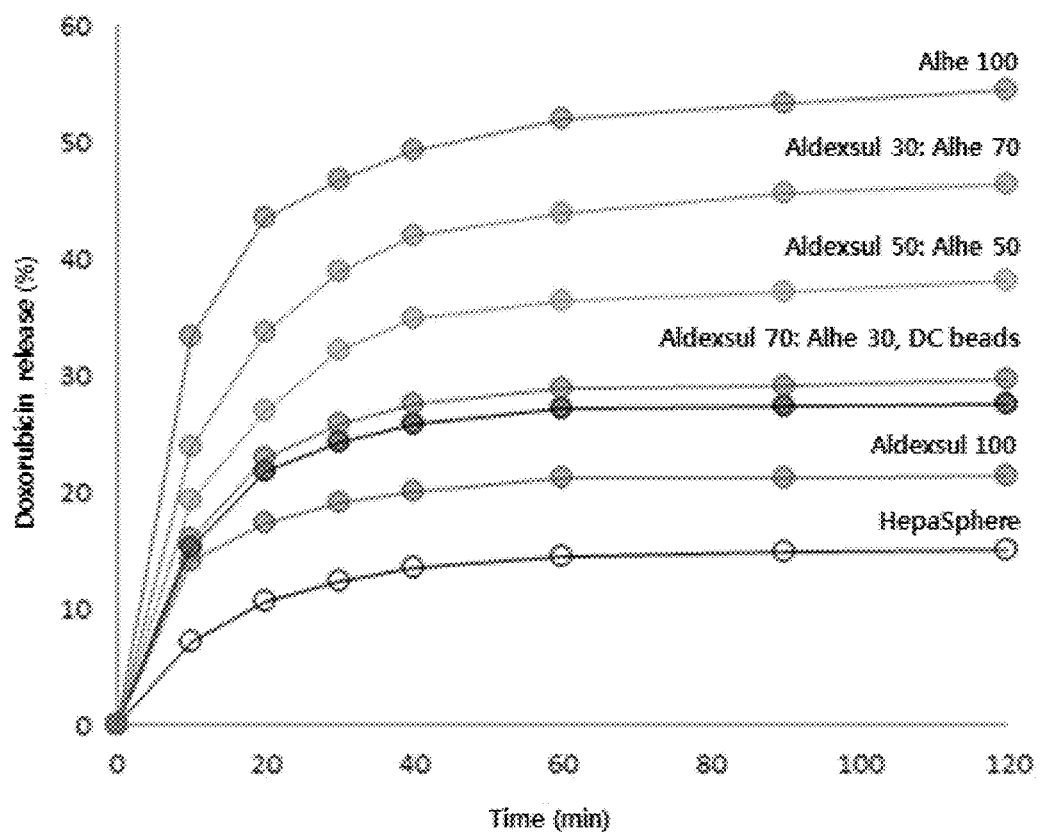
FIG. 10 is a graph showing the anticancer drug release rate over time of albumin/dextran sulfate beads (aldexsul), albumin/heparin beads (alhe), mixed beads thereof, and DC beads and HepaSphere on the market.

Test results are shown in FIGS. 1 and 5. As shown in the drawings, the doxorubicin adsorption of HepaSphere took a apparent to those skilled in the art that this description is only for a preferred embodiment and does not limit the scope of the present invention. Thus, the substantial scope of the present invention will be defined by the appended claims and equivalents thereof.

What is claimed is:
1. A composition for transarterial chemoembolization, containing:
   first biodegradable microbeads comprising: albumin, which is cross-linked to form a shape of a bead; and dextran sulfate, as an anionic polymer, contained in the albumin cross-linked product; and
   second biodegradable microbeads comprising: albumin, which is cross-linked to form a shape of a bead; and a glycosaminoglycan-based polymer, as an anionic polymer, contained in the albumin cross-linked product,
   wherein the first and second biodegradable microbeads allow an anticancer drug to be adsorbed onto a surface of the microbeads through an electrostatic attraction of the anionic polymers contained therein;

wherein the composition is capable of releasing an anticancer drug when administered into the body, the release rate of the anticancer drug being varied according to the mixing ratio of the first and second biodegradable microbeads contained in the composition; and wherein the release rate of the anticancer drug is increased according to an increased ratio of the second biodegradable microbeads to the first biodegradable microbeads.

2. The composition of claim 1, wherein the anticancer drug is an anthracycline-based anticancer drug.

3. The composition of claim 1, wherein the anticancer drug is irinotecan.

4. The composition of claim 1, wherein the glycosaminoglycan-based polymer is selected from the group consisting of chondroitin sulfate, dermatan sulfate, keratan sulfate, heparan sulfate, heparin, and hyaluronan.

5. A method for preparing a composition for transarterial chemoembolization, the method comprising: (a) preparing first biodegradable microbeads in which albumin is cross-linked and dextran sulfate is contained in the albumin cross-linked product, by cross-linking micro-sized bubbles formed by emulsifying a solution for preparing beads, in which albumin and dextran sulfate as an anionic polymer are dissolved; (b) preparing second biodegradable microbeads in which albumin is cross-linked and a glycosaminoglycan-based polymer is contained in the albumin cross-linked product, by cross-linking micro-sized bubbles formed by emulsifying a solution for preparing beads, in which albumin and a glycosaminoglycan-based polymer as an anionic polymer are dissolved; (c) adsorbing an anticancer drug onto the surface of the first and second biodegradable microbeads; and d) mixing the first and second biodegradable microbeads at a predetermined ratio, followed by packaging in a container, wherein the anticancer drug release rate of the composition is controlled according to the mixing ratio of the first and second biodegradable beads.

6. A method for treating liver cancer, the method comprising: administering a composition to a patient in need thereof the composition of claim 1.

7. The method of claim 6, wherein the microbeads are administered to the hepatic artery of the patient.

* * * * *